(12) United States Patent
Mickley et al.

(10) Patent No.: US 8,292,873 B2
(45) Date of Patent: Oct. 23, 2012

(54) CATHETER DEVICES FOR MYOCARDIAL INJECTIONS OR OTHER USES

(75) Inventors: Timothy J. Mickley, Corcoran, MN (US); Erik Sperry, Hopkinton, MA (US); Stephanie Webber, Brookline, MA (US); Chad Harris, Albertville, MN (US); Samuel J. Epstein, Watertown, MA (US); Grace Kim, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 4 days.

(21) Appl. No.: 12/187,439

(22) Filed: Aug. 7, 2008

(65) Prior Publication Data

US 2009/0143748 A1 Jun. 4, 2009

Related U.S. Application Data

(60) Provisional application No. 60/954,867, filed on Aug. 9, 2007.

(51) Int. Cl.
*A61M 25/00* (2006.01)
(52) U.S. Cl. .................................................... 604/523
(58) Field of Classification Search .......... 604/272–274, 604/523, 529, 508
See application file for complete search history.

(56) References Cited

U.S. PATENT DOCUMENTS

| | | | |
|---|---|---|---|
| 5,725,521 A * | 3/1998 | Mueller | ............................. 606/7 |
| 6,004,295 A | 12/1999 | Langer et al. | |
| 6,193,763 B1 | 2/2001 | Mackin | |
| 6,607,511 B2 | 8/2003 | Halseth | |
| 6,616,626 B2 | 9/2003 | Crank et al. | |
| 6,659,950 B2 | 12/2003 | Taheri | |
| 6,835,193 B2 * | 12/2004 | Epstein et al. | ................. 604/507 |
| 6,855,124 B1 | 2/2005 | Gonzalez | |
| 7,070,582 B2 | 7/2006 | Freyman et al. | |
| 7,097,832 B1 | 8/2006 | Kornowski et al. | |
| 7,169,127 B2 | 1/2007 | Epstein et al. | |
| 7,666,203 B2 * | 2/2010 | Chanduszko et al. | ......... 606/185 |
| 2003/0130615 A1 | 7/2003 | Tom | |
| 2004/0173222 A1 | 9/2004 | Kim | |
| 2004/0226556 A1 | 11/2004 | Deem et al. | |
| 2004/0249359 A1 | 12/2004 | Palasis et al. | |
| 2005/0038406 A1 | 2/2005 | Epstein et al. | |
| 2005/0124975 A1 | 6/2005 | Law | |
| 2005/0261667 A1 | 11/2005 | Crank et al. | |
| 2006/0206056 A1 | 9/2006 | Freyman et al. | |
| 2007/0083168 A1 | 4/2007 | Whiting et al. | |
| 2007/0106259 A1 | 5/2007 | Epstein et al. | |

(Continued)

FOREIGN PATENT DOCUMENTS

EP 0086338 8/1983

(Continued)

*Primary Examiner* — Kevin C Sirmons
*Assistant Examiner* — Imani Hayman
(74) *Attorney, Agent, or Firm* — Vidas, Arrett and Steinkraus

(57) ABSTRACT

A catheter device includes an elongate tubular housing, a cannula, and a flexible proboscis. The cannula defines a cannula lumen which is in fluid communication with a cannula exit port located adjacent the distal end of the elongate housing. The distal tip of the cannula is disposed within the cannula lumen. The cannula defines a proboscis lumen and the cannula has a proboscis exit port in fluid communication with the proboscis lumen. The proboscis exit port is located at the distal tip of the cannula. The flexible proboscis has a distal tip and is disposed within the proboscis lumen.

20 Claims, 6 Drawing Sheets

U.S. PATENT DOCUMENTS

| | | |
|---|---|---|
| 2007/0282257 A1 | 12/2007 | Schatz |
| 2007/0282267 A1 | 12/2007 | Schatz |
| 2008/0038229 A1 | 2/2008 | Minguell et al. |
| 2008/0140006 A1 | 6/2008 | Eskuri et al. |
| 2008/0281391 A1 * | 11/2008 | MacAdam et al. ........... 607/122 |

FOREIGN PATENT DOCUMENTS

| | | |
|---|---|---|
| EP | 0797957 | 10/1997 |
| WO | 0035531 | 6/2000 |

* cited by examiner

CATHETER DEVICES FOR MYOCARDIAL INJECTIONS OR OTHER USES

CROSS-REFERENCE TO RELATED APPLICATIONS

This application claims priority to U.S. Provisional Patent Application No. 60/954,867, filed Aug. 9, 2007, the entire contents of which is expressly incorporated herein by reference.

STATEMENT REGARDING FEDERALLY SPONSORED RESEARCH

Not Applicable

FIELD OF THE INVENTION

Some embodiments of the present invention relate to medical devices, and more particularly, to catheter devices for myocardial injections or other uses.

BACKGROUND

Catheters are used in a wide variety of minimally-invasive or percutaneous medical procedures. One type of catheter is an intravascular catheter, which enables a physician to remotely perform a medical procedure by inserting the catheter into the vascular system of the patient at an easily accessible location and navigating the tip of the catheter to the target site. Using catheter-guided methods, many internal sites may be remotely accessed through the patient's vascular system or other body lumen structure.

In some applications, a needle may be connected to a catheter assembly to deliver a therapeutic agent into remote sites within a patient's body. For example, in a percutaneous myocardial revascularization procedure, the inside surface of the heart is accessed by an intravascular catheter via a retrograde route through the venous system. A needle is advanced through the catheter, and the heart muscle is then injected with therapeutic agents, such as stem cells or drugs, to promote new blood vessel formation in the heart muscle.

FIG. 1 shows a PRIOR ART myocardial injection catheter 100 with an injection needle 140 positioned in the myocardium of myocardial wall 130. The beating of the heart can cause needle tip 142 to move from position A to position B relative to the myocardium. It is desirable to provide a catheter device that can deliver therapeutic or diagnostic agents to the myocardium while reducing the risk of injury.

The art referred to or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §1.72.

BRIEF SUMMARY OF THE INVENTION

In at least one embodiment, the present invention provides a catheter device comprising: an elongate tubular housing having a cannula lumen and a cannula exit port in communication with the cannula lumen, wherein the cannula exit port is located near the distal end of the elongate housing; a cannula disposed within the cannula lumen, wherein the cannula has a proboscis lumen and a proboscis exit port in communication with the proboscis lumen, and wherein the proboscis exit port is located at the distal tip of the cannula; and a flexible proboscis disposed within the proboscis lumen, the proboscis being more flexible than the cannula.

In some embodiments, the present invention provides a catheter device comprising: an elongate member comprising an elongate tubular housing, wherein the elongate housing has a proboscis lumen and an exit port in communication with the proboscis lumen; a proboscis disposed within the proboscis lumen; and an elastically deformable cushion positioned at the distal end of the elongate member, wherein the cushion includes a passageway through which the proboscis travels.

In at least one embodiment, the present invention provides methods for delivering a therapeutic or diagnostic agent into myocardium by using catheter devices of the present invention.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
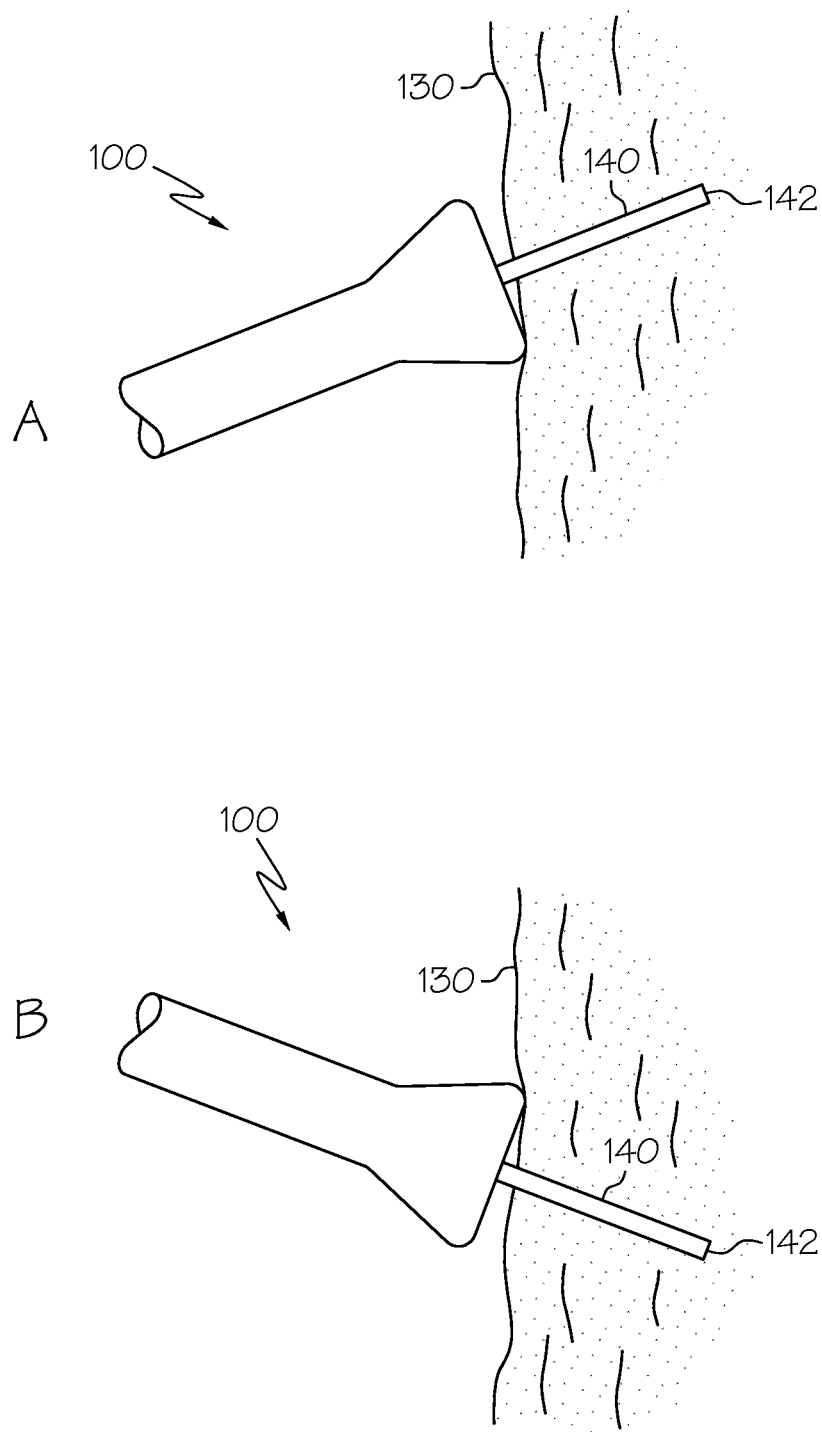
FIG. 1 shows the distal end of a PRIOR ART myocardial injection catheter with the injection needle embedded in the myocardium.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment, the present invention provides a catheter device comprising an elongate tubular housing, a cannula that is disposed within the elongate tubular housing, and a flexible proboscis that is disposed within the cannula. The elongate housing functions to deliver the cannula and the flexible proboscis to the target site at an internal site in the body. The elongate housing may be a part of a delivery catheter.

The elongate housing has a lumen for containing a cannula. At its distal end, the elongate housing also has an exit port to provide an opening for the cannula to exit from the elongate housing. The exit port may be located at the distal end or near the distal end of the elongate housing.

The cannula may exit from the elongate housing in any of various directions, depending upon the structural characteristics of the distal portion of the elongate housing, such as the location of the exit port, the path of the lumen leading to the exit port, and the shape of the distal portion of the elongate housing. For example, where the exit port is located on the distal end of the housing, the cannula may exit in a direction along the central axis of the elongate housing. In another example, where the exit port is located on the elongate housing at a location proximally near the distal end, the cannula may exit at an angle relative to the central axis of the elongate housing.

In some embodiments, the cannula may be slidable in relation to the elongate housing. In such cases, the cannula may be retracted within the elongate housing, and then advanced such that the distal end of the flexible proboscis exits from the exit port. In some cases, the cannula has a telescoping relationship to the elongate housing. In other embodiments, the axial position of the cannula is fixed in relation to the elongate housing. In such cases, the cannula may be fixed with its distal end extending out from the exit port.

The cannula has a lumen for containing the flexible proboscis. The cannula also has an exit port at its distal tip to provide an opening for the flexible proboscis to exit the cannula. The function of the cannula is to pierce through the outer layer of a tissue structure, giving the more flexible proboscis (relative to the cannula) access to the inner portions of the tissue structure. For example, the myocardial wall is one type of tissue structure for which the catheter devices of the present invention may be used. On its internal surface (facing the inner chambers of the heart), the myocardial wall is lined with a thin membrane known as the endocardium, which is a tissue structure that is relatively more durable and harder to penetrate than the myocardium. Accordingly, the cannula can be designed to pierce through the endocardium, providing a pathway for the flexible proboscis into the myocardium.

The cannula can be designed to have various shapes or structures suitable for performing the function of penetrating the outer layer of a tissue structure. For example, the distal tip of the cannula may have a sharp point or a beveled tip to enhance tissue penetration. The cannula may be made from any of various materials that provide sufficient rigidity for performing this function, such as stainless steel, nitinol, or any other suitable metallic material, or a stiff polymeric material.

In some embodiments, the flexible proboscis may be slidable in relation to the cannula. In such cases, the flexible proboscis may be retracted within the cannula, and then advanced such that the distal end of the flexible proboscis exits from the exit port on the cannula. In some cases, the flexible proboscis has a telescoping relationship to the cannula. In at least one embodiment, the axial position of the flexible proboscis is fixed relative to the cannula. In such cases, the flexible proboscis may be positioned such that its distal end extends out from the exit port on the cannula.

In at least one embodiment, to provide flexibility, the cannula may have a plurality of through-holes in the structure of the cannula. The through-holes may be in the form of slots, holes, cut-outs, perforations, and the like. The through-holes may be formed by various techniques, including micromachining or laser drilling. The flexibility of the cannula may be adjusted by varying the characteristics of the through-holes, such as the number, pattern, spacing, geometry, or dimensions of the through-holes. For example, the flexibility of the cannula may be increased by increasing the number of through-holes or increasing the size of the through-holes. In some instances, where the cannula has a plurality of through-holes, the cannula may be covered with a protective sheath, such as a polymer sheath.

The term "flexible," as used herein when referring to the cannula or the proboscis, is intended to have the meaning as understood by one of ordinary skill in the art with respect to proboscis-type elements that can be used to penetrate the myocardium. For example, flexible injection needles are known in the art (e.g., U.S. Pat. No. 6,855,124 (Gonzalez et al.) and U.S. Pat. No. 6,607,511 (Halseth et al.), the entire contents of each being expressly incorporated herein by reference). Furthermore, one of ordinary skill in the art would understand that "flexible" would exclude the numerous examples of non-flexible proboscis-type elements known in the art, such as the common stainless steel syringe needle.

In some embodiments, the cannula has myocardium-relative flexibility. "Myocardium-relative flexibility," as used herein when referring to the cannula or the proboscis, is intended to mean that the element is sufficiently flexible that relative motion between a proximal portion of the element and the myocardium (e.g., caused by external manipulation of the catheter or the beating of the heart) is not significantly translated into relative motion at the distal tip of the element when embedded in the myocardium.

In certain instances, the cannula may have myocardium-protective flexibility. "Myocardium-protective flexibility," as used herein when referring to the cannula or the proboscis, is intended to mean that the element is sufficiently flexible that there is minimal injury to the myocardium when the element is embedded in the myocardium and there is relative motion between the myocardium and the element.

In certain embodiments, the catheter device includes a mechanism for controlling the tissue penetration depth of the cannula. Various mechanisms for controlled depth penetration are known in the art, including mechanisms that use one or more stops. In some cases, the control mechanism on the catheter device can be adjustable by the operator. The catheter device can be designed to control the penetration of the cannula to any depth suitable for the particular application. For example, when used for myocardial injections, the control mechanism may allow penetration of the cannula through the endocardium, but limit penetration into the myocardium.

In some cases, the flexible proboscis may be designed to deliver a therapeutic or diagnostic agent into the target tissue. As such, the flexible proboscis may have one or more lumens and one or more apertures through which the therapeutic or diagnostic agent is delivered. The flexible proboscis may have a single aperture at its distal tip or a plurality of apertures at its distal portion.

As used herein, the term "proboscis" refers to an elongate structure that penetrates into tissue to provide and/or deliver a diagnostic or therapeutic intervention. Examples of proboscises include injection needles; injection catheters; electrodes; sensors; probes including those used for applying RF or microwave therapy, cryotherapy, or ultrasound; or optical fibers (e.g., for use in sensing, imaging, phototherapy, or laser ablation therapy, such as in transmyocardial revascularization). Depending upon the particular application, the proboscis may have any of various configurations or characteristics; for example, the proboscis may be curved or straight, hollow or solid, sharp or blunt; or for example, the transverse cross-section of the proboscis may be round, square, or triangular; or for example, the tip of the proboscis may be blunt, beveled, or sharp.

The flexible proboscis is designed to be rigid enough to penetrate into myocardial tissue without substantially kinking or collapsing, yet be flexible enough that it does not cause significant traumatic injury to the myocardium under normal operating conditions while embedded in the myocardium. In certain embodiments, the flexible proboscis is sufficiently flexible that it is unable to penetrate the epicardium, which is penetration-resistant similar to the endocardium. This feature can be useful in situations where the flexible proboscis penetrates through the thickness of the myocardium. Because the flexible proboscis is unable to penetrate the epicardium, complete perforation of the myocardial wall can be avoided.

Various factors influence the flexibility of the flexible proboscis, including its material composition (e.g., the hardness/softness of the material), its dimensions (e.g., wall thickness), and other structural characteristics (e.g., the shape of the proboscis or the combination of flexible and inflexible segments on the proboscis). One of ordinary skill in the art can select these factors in accordance with the invention to design a flexible proboscis having the desired level of flexibility. In certain embodiments, the flexible proboscis has myocardium-relative flexibility. In certain embodiments, the flexible proboscis has myocardium-protective flexibility. In certain embodiments, the catheter device includes a mechanism for controlling the tissue penetration depth of the flexible proboscis.

Figure 2A:
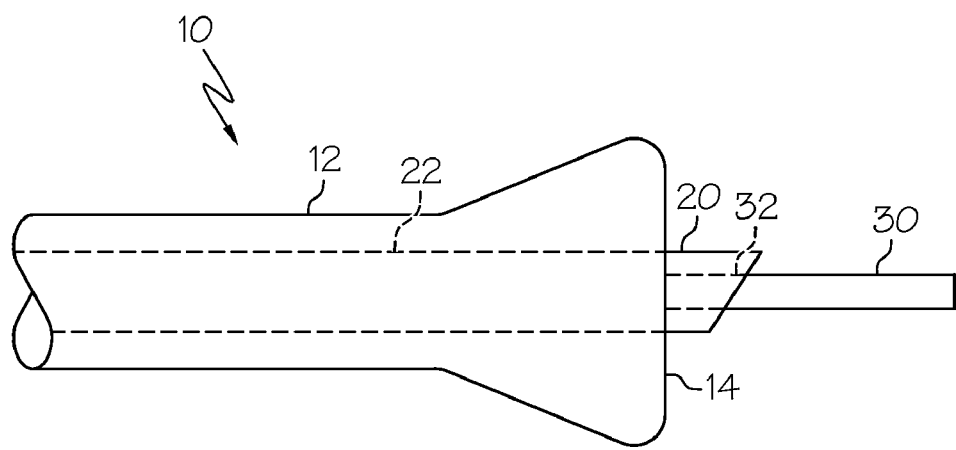
FIG. 2A shows a side view and FIG. 2B shows a perspective view of the distal portion of a catheter device according to an embodiment of the present invention.
Figure 2B:
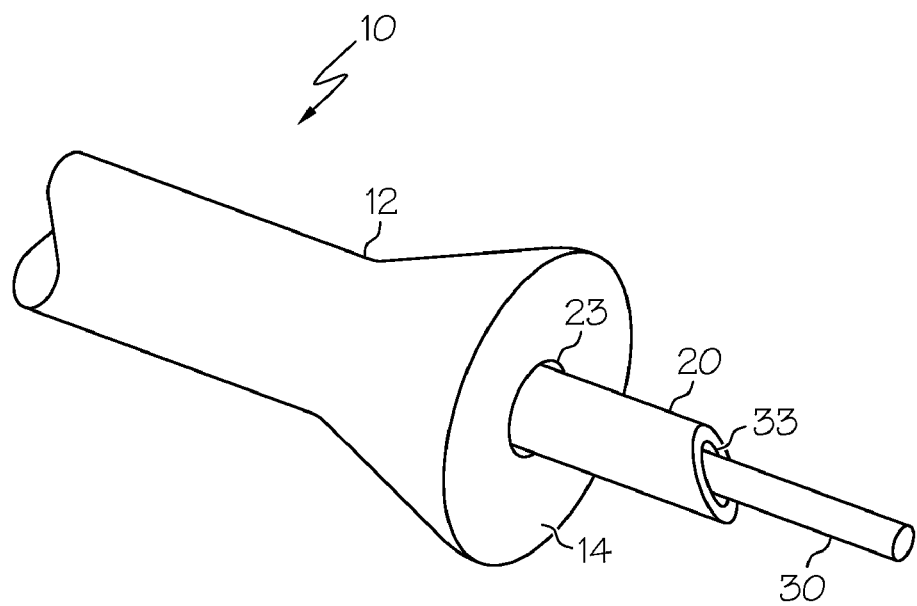

The following non-limiting examples further illustrate various embodiments of the present invention. FIGS. 2A and 2B depict a catheter device 10 according to one embodiment. Catheter device 10 comprises an elongate tubular housing 12, a cannula 20 coaxially disposed within elongate housing 12, and a flexible proboscis in the form of a flexible needle 30 coaxially disposed within cannula 20. Elongate housing 12 has a tissue contact surface 14, which engages the surface of the target site tissue. Elongate housing 12 has a cannula lumen 22 in which cannula 20 resides and a cannula exit port 23 through which cannula 20 exits. Cannula 20 is axially slidable in relation to elongate housing 12. Cannula 20 has a needle lumen 32 in which flexible needle 30 resides and a needle exit port 33 through which flexible needle 30 exits. Flexible needle 30 is axially slidable in relation to cannula 20. Cannula 20 has a sharp, beveled tip to enhance tissue penetration.

Figure 3A:
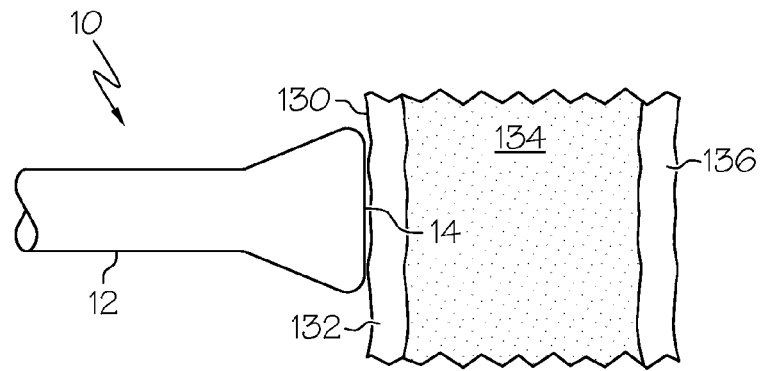
FIG. 3 demonstrates the operation of a catheter device of the present invention according to certain embodiments.
Figure 3B:
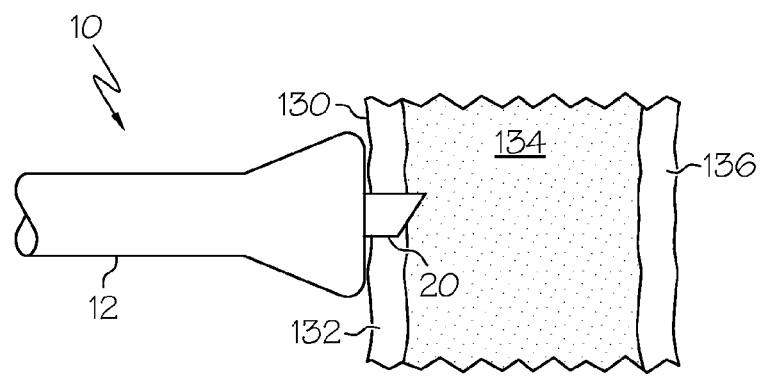
Figure 3C:
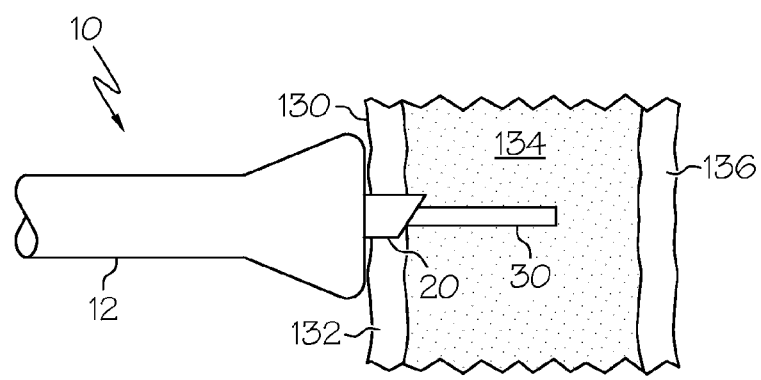

FIG. 3 demonstrates the operation of catheter device 10 when used for myocardial injections. The myocardial wall 130 is shown having the endocardium 132 lining the inside surface of the heart, the epicardium 136 lining the outside surface of the heart, and the myocardium 134 between the two layers. Referring to (A), both needle cannula 20 and flexible needle 30 are in a retracted position. Using intravascular catheterization techniques, catheter device 10 is guided through the vascular system to an internal chamber of the heart. Elongate housing 12 is positioned so that contact surface 14 engages the endocardium 132. Referring to (B), needle cannula 20 is advanced so that it penetrates through the endocardium 132. In this example, needle cannula 20 extends to a maximum distance of 1 mm beyond cannula exit port 23 (not shown). In other embodiments, the maximum distance may be selected from a range of 0.5-3 mm, but longer or shorter distances may also be chosen depending upon the application.

Referring to (C), once needle cannula 20 penetrates the endocardium 132, flexible needle 30 is advanced into the myocardium 134. In this example, flexible needle 30 extends to a maximum distance of 7 mm beyond cannula exit port 23 (not shown). In other embodiments, the maximum distance may be selected from a range of 0.5-15 mm, but longer or shorter distances may also be chosen depending upon the application. The therapeutic or diagnostic agent is then delivered to the myocardium 134 through flexible needle 30. Also, even if flexible needle 30 penetrates through the thickness of the myocardium 134, because flexible needle 30 is insufficiently rigid to penetrate the epicardium 136, a complete perforation of the myocardial wall 130 can be avoided.

Figure 4:
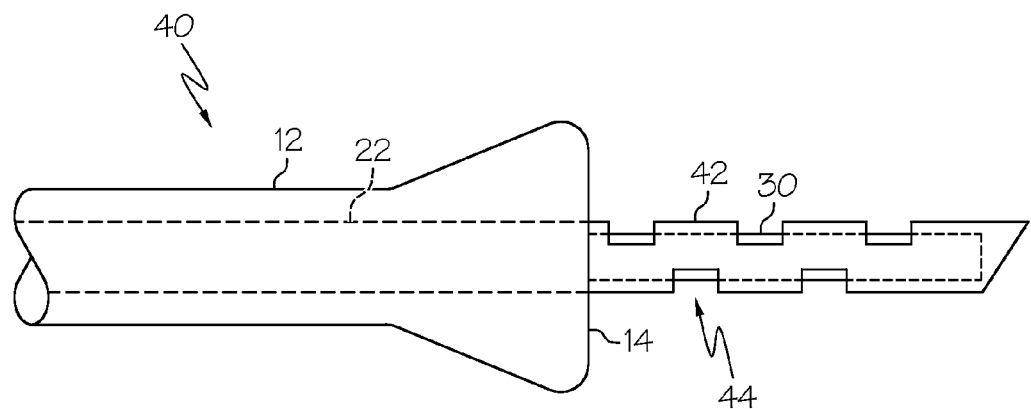
FIG. 4 shows a side view of the distal portion of a catheter device according to another embodiment.

FIG. 4 depicts a catheter device 40 according to another embodiment. Catheter device 40 comprises an elongate tubular housing 12, a needle cannula 42 disposed within elongate housing 12, and a flexible needle 30 disposed within needle cannula 42. Needle cannula 42 is axially slidable in relation to elongate housing 12, but the axial position of flexible needle 30 is fixed in relation to needle cannula 42. Needle cannula 42 has a sharp, beveled tip to enhance tissue penetration. To impart flexibility, needle cannula 42 has a plurality of slots 44 through the thickness of needle cannula 42. Various characteristics of slots 44, such as their number, pattern, spacing, geometry, or dimensions can be adjusted to achieve the desired level of flexibility in needle cannula 42.

In another aspect, the present invention provides a catheter device comprising an elongate member which comprises an elongate tubular housing. The catheter device further comprises an elastically deformable cushion located on the distal end of the elongate member and a proboscis coaxially disposed within the elongate housing. The elongate member functions to deliver the proboscis to an internal site in the body. The elongate member may be a part of a delivery catheter.

The elongate housing has a lumen for containing the proboscis. The elongate housing also has an exit port at its distal portion to provide an opening for the proboscis to exit from the elongate housing. The exit port may be located at the distal end or near the distal end of the elongate housing. The proboscis may exit from the elongate housing in any of various directions depending upon the structural characteristics of the distal portion of the elongate housing. In certain embodiments, the elongate member may further comprise a cushion seat at its distal end to facilitate engagement of the cushion with the elongate housing. The cushion seat may be positioned between the elongate housing and the cushion, and coupled to both of these elements.

In some cases, the proboscis may be designed to deliver a therapeutic or diagnostic agent into the target tissue. As such, the proboscis may have one or more lumens and one or more apertures through which the therapeutic agent is delivered. The proboscis may have a single aperture at its distal tip or a plurality of apertures at its distal portion. The proboscis may have varying degrees of stiffness or flexibility depending upon the particular application. In certain embodiments, the proboscis is slidable in relation to the elongate housing. In other embodiments, the axial position of the proboscis is fixed relative to the elongate housing.

An elastically deformable cushion is located on the distal end of the elongate member. The cushion and the elongate member may be a single unitary structure or the two components may be separate units that are coupled together. The elastically compressible cushion includes a passageway through which the proboscis travels. The passageway may be any passage by which the proboscis travels through the cushion, such as a channel, a tunnel, or simply an opening in the cushion (e.g., a central hole in a doughnut-shaped cushion).

The cushion is designed to be deformable in response to compressive force which may be applied through the elongate housing or by the tissue surface. The term "deformable," as used herein when applied to a cushion, is intended to mean that the cushion can be deformed under compressive forces encountered by the cushion during an injection procedure. Information about these forces, such as quantity and direction, are known or are readily available to one of ordinary skill in the art. As used herein, "elastically deformable" is intended to mean that the cushion will substantially return to its original shape and dimensions when the compressive force is released. This feature may allow the cushion to be retracted back into a delivery catheter.

The elastically deformable cushion may be constructed in any of various ways. For example, the cushion may be formed of an elastomeric material, such as silicone, polyurethane foam, or other elastomer-type of material. In another example, the cushion may be a bladder, balloon, or other enclosure filled with gel, gas, or liquid. The cushion may have any suitable shape or form, such as a collar, cylinder, washer, ring, doughnut, hub, sphere, etc.

The cushion has a contact surface which engages the target tissue. The contact surface may be on any aspect of the cushion, including the sides, edges, or distal face of the cushion. If the cushion does not have defined faces (such as in a sphere), the contact surface is that portion of the surface of the cushion that engages the target tissue. The cushion functions to reduce the amount of trauma to the target tissue caused by the catheter device. In some cases, the contact surface has a surface area of at least 0.8 mm$^2$ to reduce the amount of trauma to the target tissue upon initial contact. The cushion may also perform this function by deforming under compressive forces that are experienced in catheter-guided myocardial injection procedures. When the cushion deforms, the area of the contact surface by which the cushion engages the tissue increases, thereby reducing the contact pressure.

Various characteristics of the cushion, such as its shape, dimensions, or material composition may be adjusted to provide the desired increase in contact surface area under the compressive forces. The increase in the area of contact surface can range from 1.5 to 20-fold under compressive forces ranging from 0.1 to 1 lb; and in some cases, the increase in the area of contact surface can range from 3 to 15-fold; and in some cases, the increase in the area of contact surface can range from 6 to 10-fold. An increase in the contact surface area will directly reduce the force per unit area, which in turn, reduces the potential for penetration. Thus it is believed that an increase in the amount of contact surface area in these ranges, from an initial contact surface area of at least 0.8 mm$^2$, would be sufficient to reduce the amount of trauma to the myocardium during a catheter-guided myocardial injection procedure. Depending upon the application, other values representing the increase in the area of contact surface and the compressive force are also possible.

In some cases, the cushion is sufficiently compliant such that the contact surface conforms to the target tissue surface. For example, the contact surface may conform to the internal surface of the heart, which may be characterized by its curvature, shape, geometry, folds, and trabeculae structures. By conforming to the target tissue surface, the contact surface area increases. Thus, it is believed that a cushion that conforms to the internal surface of the heart may reduce the amount of trauma to the myocardium during a catheter-guided myocardial injection procedure.

The cushion may be designed such that it has no sharp corners that could cause damage to tissue. For example, the distal face of the cushion could transition to the side face of the cushion at a rounded corner. In this way, if the device approaches the tissue at an angle, the cushion does not present a sharp corner to the tissue.

In certain embodiments, the catheter device may further comprise a mechanism for limiting the penetration depth of the proboscis. Various such mechanisms are known in the art and, based on the disclosure, one of ordinary skill in the art would know how to adapt such mechanisms to be used in the catheter devices of the present invention. For example, one or more stops can be positioned on the proboscis and/or the cushion in various arrangements to interact with each other. These stops can form a single unitary structure with the proboscis or cushion, or the components may be separate units that are coupled together.

Figure 5:
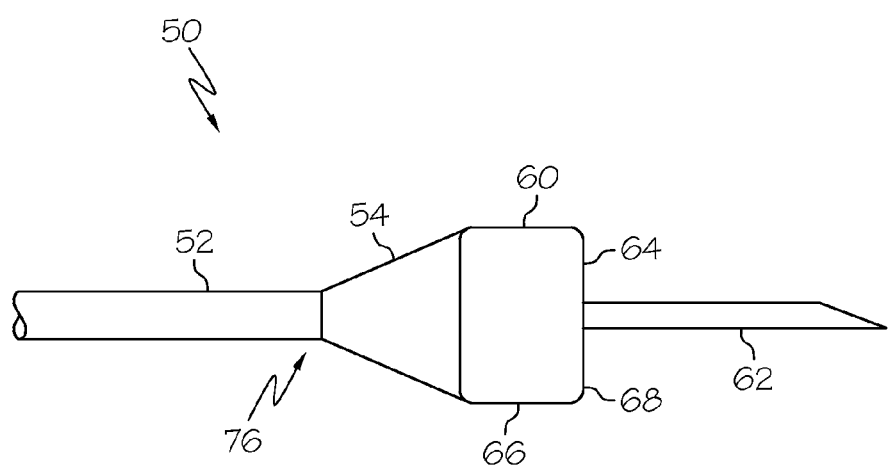
FIG. 5 shows a side view of the distal portion of a catheter device according to yet another embodiment.

The following non-limiting examples further illustrate various embodiments of the present invention. FIG. 5 depicts a catheter device 50 according to yet another embodiment. Catheter device 50 comprises an elongate member 76, which comprises an elongate housing 52. An injection needle 62 is coaxially disposed within elongate housing 52. Elongate member 76 further comprises a cushion seat 54 positioned at the distal end of elongate housing 52. Cushion seat 54 is coupled to a cushion 60 and elongate housing 52. On its distal face, cushion 60 has a contact surface 64 for engaging the target site tissue. In this example, contact surface 64 transitions to the side aspect 66 of cushion 60 at a rounded corner 68.

In this embodiment, the axial position of injection needle 62 is fixed relative to elongate housing 52 such that injection needle 62 extends beyond the distal end of cushion 60. In other embodiments, the axial position of injection needle 62 is fixed relative to elongate housing 52 such that injection needle 62 remains fully inside cushion 60. When cushion 60 is compressed, injection needle 62 is exposed. In other embodiments, injection needle 62 may be slidable within elongate housing 52 such that injection needle 62 has a telescoping relationship to elongate housing 52.

Figure 6A:
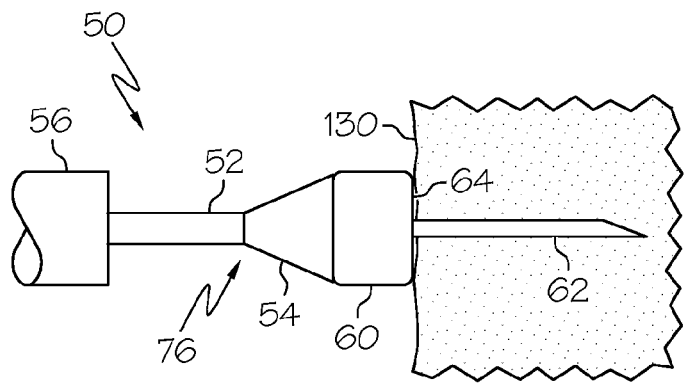
FIG. 6 demonstrates the operation of a catheter device of the present invention according to certain embodiments.
Figure 6B:
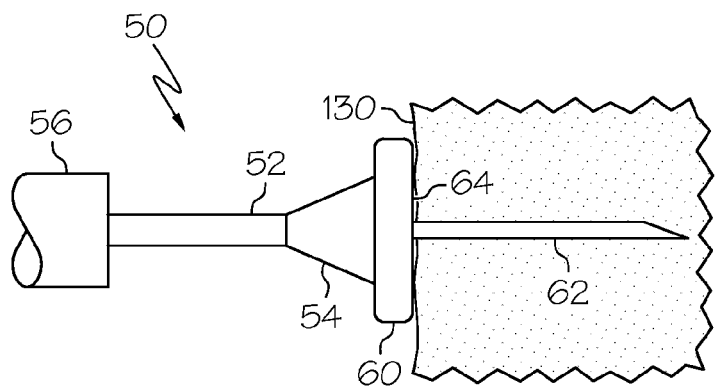
Figure 6C:
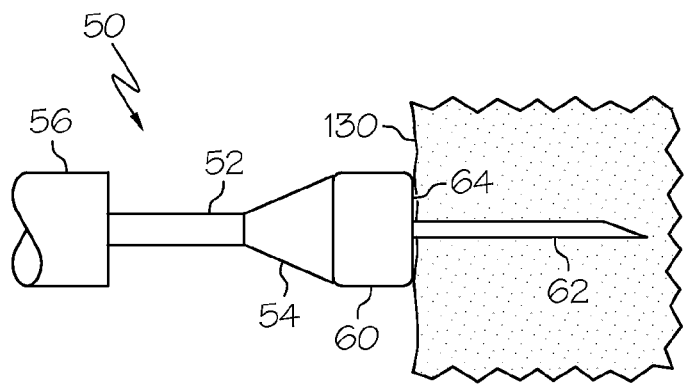

FIG. 6 demonstrates the operation of catheter device 50 when used for myocardial injections. Referring to (A), a catheter 56 is used to deliver catheter device 50 to an internal chamber of the heart. Catheter device 50 is then manipulated such that injection needle 62 pierces into the myocardial wall 130. Referring to (B), as compressive force is applied to catheter device 50, cushion 60 deforms by expanding radially, causing an increase in the area of contact surface 64. Referring to (C), when the compressive force is removed, cushion 60 returns to its original shape and dimensions, allowing cushion 60 to be retracted back into catheter 56.

Figure 7A:
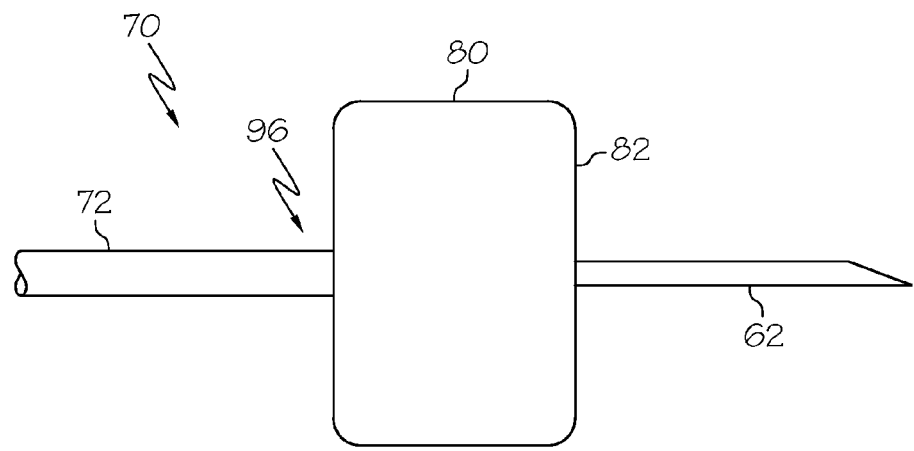
FIG. 7A shows a side view and FIG. 7B shows a partial cut-away and cross-section view of the distal portion of a catheter device according to yet another embodiment.
Figure 7B:
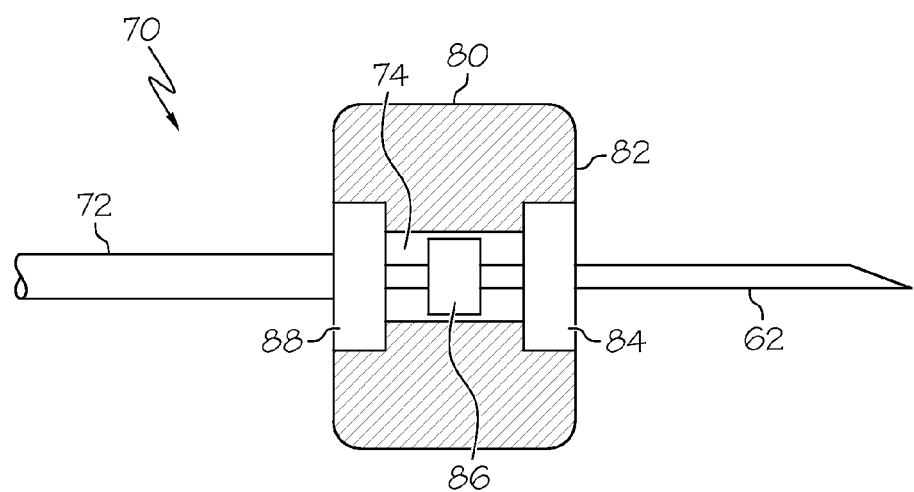

FIGS. 7A (side view) and 7B (side view with a portion of cushion 80 cut away) depict a catheter device 70 according to yet another embodiment. Catheter device 70 comprises an elongate member 96, which comprises an elongate housing 72. An injection needle 62 is coaxially disposed within elongate housing 72 and travels through a cushion 80 via a passageway 74. Elongate member 96 further comprises a cushion seat 88 positioned at the distal end of elongate housing 72. Cushion seat 88 is coupled to elongate housing 72 and to cushion 80. On its distal face, cushion 80 has a contact surface 82 for engaging the target site tissue.

In this particular embodiment, the axial position of injection needle 62 is fixed relative to elongate housing 72. Also in this particular embodiment, catheter device 70 includes a controlled depth penetration mechanism. The mechanism includes a first stop 86 affixed to injection needle 62 and a second stop 84 affixed to or adjacent the distal end of cushion 80. In operation, as cushion 80 is compressed against the myocardial wall, the gap between first stop 86 and second stop 84 closes (by first stop 86 moving towards second stop 84, or vice versa). When the two stops come into contact, further advancement of injection needle 62 into the myocardium is prevented. The positions of stops 84 and 86 are selected according to the maximum amount of needle penetration depth desired, which may depend upon the type of myocardium that is being treated (e.g., normal, hypertrophied, dilated). In certain embodiments, the stops are positioned such that the maximum needle penetration depth has a low risk of perforating a myocardium of normal thickness. In some instances, the stops are positioned such that the maximum penetration depth of injection needle 62 is in the range of 1-10 mm, but other ranges are also possible depending upon the application.

The catheter devices of the present invention may have any of various applications in catheter-guided interventions. For example, in addition to myocardial injections, the catheter devices of the present invention may be used for delivering electrical stimulation to the myocardium via electrodes. Also, the catheter devices of the present invention may be used for other target sites in the body, such as the blood vessels or the gastrointestinal tract.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A catheter device comprising:
   an elongate tubular housing having a distal end and defining a cannula lumen, the cannula lumen being in fluid communication with a cannula exit port, wherein the cannula exit port is located adjacent the distal end of the elongate housing;
   a cannula, the cannula having a distal tip and being disposed within the cannula lumen, wherein the cannula defines a proboscis lumen, the cannula having a proboscis exit port in fluid communication with the proboscis lumen, and wherein the proboscis exit port is located at the distal tip of the cannula;
   and a proboscis, the proboscis being more flexible than the cannula, the proboscis having a distal tip and being disposed within the proboscis lumen wherein at least one of the cannula and the proboscis has a fixed axial position with the cannula being fixed in relation to the housing and the proboscis being fixed in relation to the cannula.

2. The device of claim 1, wherein the cannula exit port is located at the distal end of the elongate housing.

3. The device of claim 1, wherein the flexible proboscis is made of a polymeric material.

4. The device of claim 1, wherein the flexible proboscis is a flexible injection needle.

5. The device of claim 1, wherein the cannula is slidable along a longitudinal axis in relation to the elongate housing, and wherein in an extended state the distal tip of the cannula extends distally beyond the cannula exit port.

6. The device of claim 5, wherein the distal tip of the cannula extends distally beyond the cannula exit port in the range of 0.5-3 mm.

7. The device of claim 1, wherein the flexible proboscis is slidable along a longitudinal axis in relation to the cannula, and wherein in an extended state the distal tip of the proboscis extends distally beyond the proboscis exit port.

8. The device of claim 7 wherein the distal tip of the flexible proboscis extends distally beyond the cannula exit port in the range of 0.5-15 mm.

9. The device of claim 1, wherein the cannula is fixed in relation to the elongate housing, and wherein the distal tip of the cannula extends distally beyond the cannula exit port.

10. The device of claim 9, wherein the distal tip of the cannula extends distally past the cannula exit port a distance in the range of 0.5-15 mm.

11. The device of claim 1, wherein the cannula is flexible.

12. A catheter device comprising:
    an elongate member having a distal end and comprising an elongate tubular housing, wherein the elongate housing defines a proboscis lumen, the proboscis lumen being in fluid communication with a proboscis exit port;
    a proboscis having a proboscis distal tip and being disposed within the proboscis lumen; and
    an elastically deformable cushion positioned at the distal end of the elongate member, wherein the cushion defines a passageway through which the proboscis travels, and wherein the cushion has a distal end and a contact surface for engaging a target site, the distal end of the cushion defining an opening for the passageway, the distal end of the cushion being cushion material except for the opening for the passageway.

13. The device of claim 12, wherein the cushion comprises an elastomeric material.

14. The device of claim 12, wherein the proboscis is fixed longitudinally relative to the elongate housing, wherein the proboscis distal tip extends beyond the distal end of the cushion.

15. The device of claim 12, wherein the proboscis is fixed longitudinally relative to the elongate housing and wherein in a first state the proboscis distal tip is disposed within the cushion and in a second state the proboscis distal tip extends distally beyond the distal end of the cushion.

16. The device of claim 12, wherein the distal end of the elongate member comprises a cushion seat, and wherein the cushion seat is engaged to the cushion.

17. The device of claim 12, wherein when the cushion is in a first state, the contact surface has a first area and when the cushion is in a second state the contact surface has a second area that is 1.5 to 20 fold greater than the first area.

18. The device of claim 12, wherein the cushion has a form selected from the group comprising a collar, a cylinder, a ring, a doughnut, and a sphere.

19. The device of claim 12, further comprising a first stop and a second stop, the first stop being engaged to a portion of the proboscis disposed within the passageway defined by the cushion, the second stop being distal to the first stop, wherein when the cushion is in a first state the first stop and the second stop are separated by a first distance and when the cushion is in a second state the first stop is in contact with the second stop.

20. The device of claim 12, the elongate member defining only one lumen, the one lumen being the proboscis lumen, the proboscis lumen being in communication with the passageway defined by the cushion.

* * * * *